United States Patent
Künzler et al.

(10) Patent No.: US 6,958,169 B2
(45) Date of Patent: Oct. 25, 2005

(54) SURFACE TREATMENT OF MEDICAL DEVICE

(75) Inventors: Jay F. Künzler, Canandaigua, NY (US); Joseph A. McGee, DeWitt, NY (US); Joseph C. Salamone, Fairport, NY (US); David E. Seelye, North Chili, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 235 days.

(21) Appl. No.: 10/321,949

(22) Filed: Dec. 17, 2002

(65) Prior Publication Data

US 2004/0116310 A1 Jun. 17, 2004

(51) Int. Cl.[7] .......................... A61L 31/10; A61L 27/08; G02C 7/04
(52) U.S. Cl. .................. 427/2.1; 427/2.24; 427/2.12; 427/2.28; 427/430.1; 427/445; 351/160 R; 351/160 H; 510/115; 510/161; 510/475
(58) Field of Search ................................ 427/2.1, 2.24, 427/2.12, 2.28, 430.1, 445; 351/160 R, 160 H; 510/115, 161, 475

(56) References Cited

U.S. PATENT DOCUMENTS

| | | | |
|---|---|---|---|
| 4,055,378 A | 10/1977 | Fenebert et al. | 351/160 |
| 4,122,942 A | 10/1978 | Wolfson | 206/5.1 |
| 4,136,250 A | 1/1979 | Mueller et al. | 528/29 |
| 4,143,949 A | 3/1979 | Chen | 351/160 |
| 4,153,641 A | 5/1979 | Deichert et al. | 260/827 |
| 4,168,112 A | 9/1979 | Ellis et al. | 351/160 |
| 4,214,014 A | 7/1980 | Hofer et al. | 427/40 |
| 4,312,575 A | 1/1982 | Peyman et al. | 351/160 |
| 4,321,261 A | 3/1982 | Ellis et al. | 424/180 |
| 4,436,730 A | 3/1984 | Ellis et al. | 424/180 |
| 4,632,844 A | 12/1986 | Yanagihara et al. | 427/38 |
| 4,734,475 A | 3/1988 | Goldenbert et al. | 526/273 |
| 4,740,533 A | 4/1988 | Su et al. | 523/106 |
| 4,910,277 A | 3/1990 | Bambury et al. | 526/260 |
| 5,034,461 A | 7/1991 | Lai et al. | 525/100 |
| 5,070,215 A | 12/1991 | Bambury et al. | 556/418 |
| 5,260,000 A | 11/1993 | Nandu et al. | 264/2.1 |
| 5,310,779 A | 5/1994 | Lai | 524/588 |
| 5,358,995 A | 10/1994 | Lai et al. | 524/547 |
| 5,387,662 A | 2/1995 | Kunzler et al. | 526/245 |
| 5,397,848 A | 3/1995 | Yang et al. | 525/477 |
| 5,449,729 A | 9/1995 | Lai | 526/286 |
| 5,512,205 A | 4/1996 | Lai | 252/182.14 |
| 5,610,252 A | 3/1997 | Bambury et al. | 526/279 |
| 5,616,757 A | 4/1997 | Bambury et al. | 556/419 |
| 5,700,559 A | 12/1997 | Sheu et al. | 428/319.7 |
| 5,705,583 A | 1/1998 | Bowers et al. | 526/277 |
| 5,708,094 A | 1/1998 | Lai et al. | 525/296 |
| 5,710,302 A | 1/1998 | Kunzler et al. | 556/434 |
| 5,714,557 A | 2/1998 | Kunzler et al. | 526/279 |
| 5,807,636 A | 9/1998 | Sheu et al. | 428/403 |
| 5,908,906 A | 6/1999 | Kunzler et al. | 526/279 |
| 6,428,839 B1 * | 8/2002 | Kunzler et al. | 427/2.1 |
| 2004/0116310 A1 * | 6/2004 | Kunzler et al. | 510/115 |

FOREIGN PATENT DOCUMENTS

| | | |
|---|---|---|
| EP | 0127321 A1 | 12/1984 |
| EP | 0963761 | 12/1999 |
| EP | 1060753 A2 | 12/2000 |
| GB | 1480880 | 7/1977 |
| WO | WO 95/04609 | 2/1995 |
| WO | WO 96/31792 | 10/1996 |
| WO | WO 0142846 A1 | 6/2001 |

OTHER PUBLICATIONS

Lai, Yu–Chin, "The Role of Bulky Polysiloxanylalkyl Methacryates in Polyurethane–Polysiloxane Hydrogels", Journal of Applied Polymer Science, vol. 60, 1193–1199 (1996).
Advances in Polymer Science, published by Springer–Verlag, Editor H.J. Cantwo, et al., V45, 1982, pp. 17–63.

* cited by examiner

Primary Examiner—Brian P. Mruk
(74) Attorney, Agent, or Firm—John E. Thomas

(57) ABSTRACT

A method for improving the wettability of a medical device involves: (a) providing a medical device formed from a monomer mixture comprising a hydrophilic device-forming monomer including a copolymerizable group and an electron donating moiety, and a second device-forming monomer including a copolymerizable group and a reactive functional group; and (b) contacting a surface of the medical device with a wetting agent including a proton donating moiety reactive with the functional group provided by the second lens-forming monomer and that complexes with the electron donating moiety provided by the hydrophilic lens-forming monomer.

16 Claims, No Drawings

SURFACE TREATMENT OF MEDICAL DEVICE

FIELD OF THE INVENTION

The present invention is directed to the surface treatment of medical devices including ophthalmic lenses such as contact lenses and intraocular lenses, stents, implants and catheters. In particular, the present invention is directed to a simple, low cost method of modifying the surface of a medical device to increase its wettability.

BACKGROUND

Medical devices such as ophthalmic lenses can generally be sub-divided into two major classes, namely hydrogels and non-hydrogels. Non-hydrogels do not absorb appreciable amounts of water, whereas hydrogels can absorb and retain water in an equilibrium state. With respect to silicone medical devices, both non-hydrogel and hydrogel silicone medical devices tend to have relatively hydrophobic, non-wettable surfaces that have a high affinity for lipids. This problem is of particular concern with contact lenses.

Those skilled in the art have long recognized the need for modifying the surface of silicone ophthalmic devices, such as contact lenses and intraocular lenses, so that they are compatible with the eye. It is known that, in general, increased hydrophilicity of a contact lens surface improves the wettability of the contact lenses. This in turn is associated with improved wear comfort of contact lenses. Additionally, the surface of the lens can affect the lens's susceptibility to deposition, particularly the deposition of proteins and lipids from the tear fluid during lens wear. Accumulated deposition can cause eye discomfort or even inflammation. In the case of extended wear lenses (i.e., lenses used without daily removal of the lens before sleep), the surface is especially important, since extended wear lens must be designed for high standards of comfort and biocompatibility over an extended period of time.

Silicone lenses have been subjected to plasma surface treatment to improve their surface properties, for example, surfaces have been rendered more hydrophilic, deposit-resistant, scratch-resistant, or otherwise modified. Examples of previously-disclosed plasma surface treatments include subjecting contact lens surfaces to a plasma comprising: an inert gas or oxygen (see, for example, U.S. Pat. Nos. 4,055,378; 4,122,942; and 4,214,014); various hydrocarbon monomers (see, for example, U.S. Pat. No. 4,143,949); and combinations of oxidizing agents and hydrocarbons such as water and ethanol (see, for example, WO 95/04609 and U.S. Pat. No 4,632,844). U.S. Pat. No. 4,312,575 to Peyman et al. discloses a process for providing a barrier coating on a silicone or polyurethane lens by subjecting the lens to an electrical glow discharge (plasma) process conducted by first subjecting the lens to a hydrocarbon atmosphere followed by subjecting the lens to oxygen during flow discharge, thereby increasing the hydrophilicity of the lens surface.

U.S. Pat. Nos. 4,168,112, 4,321,261 and 4,436,730, all issued to Ellis et al., disclose methods for treating a charged contact lens surface with an oppositely charged ionic polymer to form a polyelectrolyte complex on the lens surface that improves wettability.

U.S. Pat. No. 5,397,848 to Yang et al. discloses a method of incorporating hydrophilic constituents into silicone polymer materials for use in contact and intra-ocular lenses.

U.S. Pat. Nos. 5,700,559 and 5,807,636, both to Sheu et al., disclose hydrophilic articles (for example, contact lenses) comprising a substrate, an ionic polymeric layer on the substrate and a disordered polyelectrolyte coating ionically bonded to the polymeric layer.

U.S. Pat. No. 5,705,583 to Bowers et al. discloses biocompatible polymeric surface coatings. The polymeric surface coatings disclosed include coatings synthesized from monomers bearing a center of positive charge, including cationic and zwitterionic monomers.

European Patent Application EP 0 963 761 A1 discloses biomedical devices with coatings that are said to be stable, hydrophilic and antimicrobial, and which are formed using a coupling agent to bond a carboxyl-containing hydrophilic coating to the surface by ester or amide linkages.

U.S. Pat. No. 4,734,475 to Goldenberg et al. discloses a contact lens made from a hydrophobic addition polymer incorporating between about 0.5 and about 30% weight oxirane substituted units in the backbone. The oxirane substituted units are reactive with a water soluble reactive organic amine, alcohol, thiol, urea or thiourea or a sulfite, bisulfite or thiosulfite.

U.S. Pat. No. 6,428,839 to Kunzler et al. discloses a method for improving the wettability of a medical device that overcomes drawbacks of various prior approaches. This method involves (a) providing a medical device that has not been subjected to a surface oxidation treatment, and (b) contacting a surface of the medical device with a wetting agent solution that preferably includes a polymer or copolymer of (meth)acrylic acid, whereby the polymer or copolymers of meth(acrylic) acid forms a complex with the hydrophilic monomer on the contact lens surface without a surface oxidation treatment step and without the addition of a coupling agent.

SUMMARY OF THE INVENTION

The present invention is directed to a method for improving the wettability of a medical device, comprising the steps of:

(a) providing a medical device formed from a monomer mixture comprising a hydrophilic device-forming monomer including a copolymerizable group and an electron donating moiety, and a second device-forming monomer including a copolymerizable group and a reactive functional group; and (b) contacting a surface of the medical device with a wetting agent including a proton donating moiety reactive with the functional group provided by the second lens-forming monomer and that complexes with the electron donating moiety provided by the hydrophilic lens-forming monomer.

According to preferred embodiments, the copolymerizable groups of the device-forming monomers are ethylenically unsaturated groups so that these monomers copolymerize with one another by a free-group polymerization process.

Preferably, the reactive functional group of the second device-forming monomer is an epoxy group. Preferably, the proton donating moiety of the wetting agent is provided by a polymer containing carboxylic acid functionality, such as a polymer containing poly(acrylic acid) (PAA). Particularly preferred polymers are characterized by acid contents of at least about 30 mole percent, preferably at least about 40 mole percent.

Similar to U.S. Pat. No. 6,428,839, the method of the invention requires neither a surface oxidation treatment step nor the addition of a coupling agent. The term "coupling agent" means an entity other than the medical device or the wetting agent coating material that forms a linkage between the surface of the medical device and the hydrophilic coating material. However, the coatings provided by this invention are believed to be more durable, and more stable when stored in non-acid solutions, than the coatings of U.S. Pat. No. 6,428,839.

DETAILED DESCRIPTION OF THE INVENTION

The method of the present invention is useful with biocompatible materials including both soft and rigid materials commonly used for ophthalmic lenses, including contact lenses. The preferred substrates are hydrogel materials, especially silicone hydrogel materials. In the case of ophthalmic lenses, the device-forming monomers may be referred to herein as lens-forming monomers.

Hydrogels in general are a well-known class of materials that comprise hydrated, crosslinked polymeric systems containing water in an equilibrium state. Accordingly, hydrogels are copolymers prepared from hydrophilic monomers. In the case of silicone hydrogels, the hydrogel copolymers are generally prepared by polymerizing a mixture containing at least one device-forming silicone-containing monomer and at least one device-forming hydrophilic monomer. Either the silicone-containing monomer or the hydrophilic monomer functions as a crosslinking agent (a crosslinker being defined as a monomer having multiple polymerizable functionalities) or a separate crosslinker may be employed. Silicone hydrogels typically have a water content between about 10 to about 80 weight percent.

Suitable device-forming hydrophilic monomers include those monomers that, once polymerized, can form a complex with the wetting agent, for example, the wetting agent containing carboxylic acid groups. Accordingly, the device-forming hydrophilic monomers include an electron donating moiety that complexes with the proton donating moiety of the wetting agent. Additionally, the hydrophilic monomers include a copolymerizable group, such as an ethylenically unsaturated group, that copolymerizes with the copolymerizable groups of other device-forming monomers.

Examples of useful device-forming hydrophilic monomers include: amides such as N,N-dimethylacrylamide and N,N-dimethylmethacrylamide; cyclic lactams such as N-vinyl-2-pyrrolidone; and (meth)acrylated poly(alkene glycols), such as poly(diethylene glycols) of varying chain length containing monomethacrylate or dimethacrylate end caps. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277, the disclosures of which are incorporated herein by reference. Other suitable hydrophilic monomers will be apparent to one skilled in the art. For example, 2-hydroxyethylmethacrylate (Hema) is a well-known hydrophilic monomer that may be used in admixture with the aforementioned hydrophilic monomers having relatively strong proton donating moieties.

The device-forming monomer mixtures also include the second device-forming monomer including a copolymerizable group and a reactive functional group. The copolymerizable group is preferably an ethylenically unsaturated group, such that this device-forming monomer copolymerizes with the hydrophilic device-forming monomer and any other device-forming monomers in the initial device-forming monomer mixture. Additionally, this second monomer includes a reactive functional group that reacts with the complementary reactive group of the wetting agent. In other words, after the device is formed by copolymerizing the device-forming monomer mixture, the reactive functional groups provided by the second device-forming monomers remain to react with the complementary reactive proton donating moieties of the wetting agent.

Preferred reactive groups of the second device-forming monomers include epoxide groups. Accordingly, preferred second device-forming monomers are those that include both an ethylenically unsaturated group (that permits the monomer to copolymerize with the hydrophilic device-forming monomer) and the epoxide group (that does not react with the hydrophilic device-forming monomer but remains to react with the wetting agent). Examples include glycidyl methacrylate, glycidyl acrylate, glycidyl vinylcarbonate, glycidyl vinylcarbamate, and 4-vinyl-1-cyclohexene-1,2-epoxide.

As mentioned, one preferred class of medical device substrate materials are silicone hydrogels. In this case, the initial device-forming monomer mixture further comprises a silicone-containing monomer.

Applicable silicone-containing monomeric materials for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995.

Examples of applicable silicon-containing monomers include bulky polysiloxanylalkyl (meth)acrylic monomers. An example of bulky polysiloxanylalkyl (meth)acrylic monomers are represented by the following Formula I:

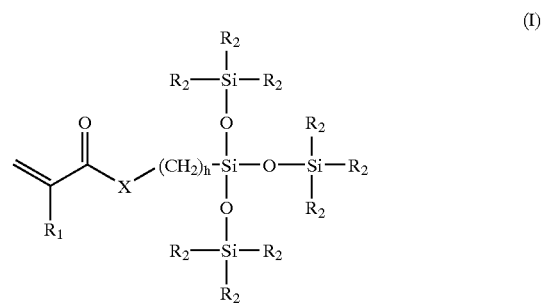

(I)

wherein:

X denotes —O— or —NR—;

each $R_1$ independently denotes hydrogen or methyl;

each $R_2$ independently denotes a lower alkyl radical, phenyl radical or a group represented by

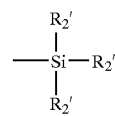

wherein each $R'_2$, independently denotes a lower alkyl or phenyl radical; and h is 1 to 10.

One preferred bulky monomer is methacryloxypropyl tris(trimethyl-siloxy)silane or tris(trimethylsiloxy) silylpropyl methacrylate, sometimes referred to as TRIS.

Another class of representative silicon-containing monomers includes silicone-containing vinyl carbonate or vinyl carbamate monomers such as: 1,3-bis[4-vinyloxycarbonyloxy)but-1-yl]tetramethyl-disiloxane; 3-(trimethylsilyl)propyl vinyl carbonate; 3-(vinyloxycarbonylthio)propyl-[tris(trimethylsiloxy)

silane]; 3-[tris(trimethylsiloxy)silyl]propyl vinyl carbamate; 3-[tris(trimethylsiloxy)silyl]propyl allyl carbamate; 3-[tris(trimethylsiloxy)silyl]propyl vinyl carbonate; t-butyldimethylsiloxyethyl vinyl carbonate; trimethylsilylethyl vinyl carbonate; and trimethylsilylmethyl vinyl carbonate.

An example of silicon-containing vinyl carbonate or vinyl carbamate monomers are represented by Formula II:

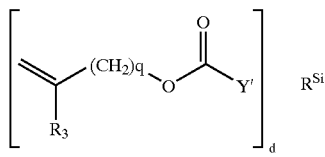
(II)

wherein:

Y' denotes —O—, —S— or —NH—;

$R^{Si}$ denotes a silicone-containing organic radical;

$R_3$ denotes hydrogen or methyl;

d is 1,2,3 or 4; and q is 0 or 1.

Suitable silicone-containing organic radicals $R^{Si}$ include the following:

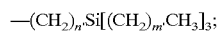

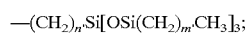

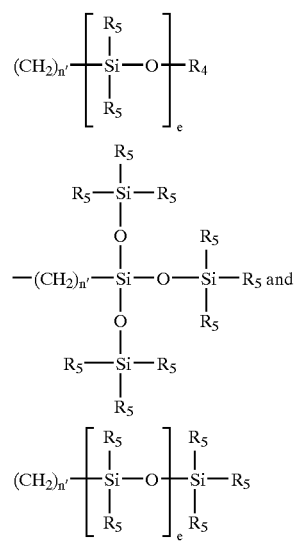

wherein:

$R_4$ denotes

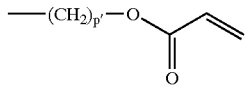

wherein p' is 1 to 6;

$R_5$ denotes an alkyl radical or a fluoroalkyl radical having 1 to 6 carbon atoms;

e is 1 to 200; n' is 1,2,3 or 4; and m' is 0, 1, 2, 3, 4 or 5.

An example of a particular species within Formula II is represented by Formula III.

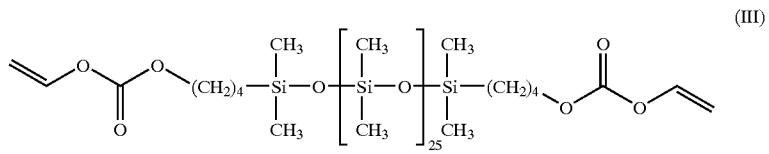
(III)

Another class of silicon-containing monomers includes polyurethane-polysiloxane macromonomers (also sometimes referred to as prepolymers), which may have hard-soft-hard blocks like traditional urethane elastomers. They may be end-capped with a hydrophilic monomer such as HEMA. Examples of such silicone urethanes are disclosed in a variety or publications, including Lai, Yu-Chin, "The Role of Bulky Polysiloxanylalkyl Methacryates in Polyurethane-Polysiloxane Hydrogels," *Journal of Applied Polymer Science*, Vol. 60, 1193–1199 (1996). PCT Published Application No. WO 96/31792 discloses examples of such monomers, which disclosure is hereby incorporated by reference in its entirety. Further examples of silicone urethane monomers are represented by Formulae IV and V:

$$E(*D*A*D*G)_a*D*A*D*E'; \text{ or} \quad (IV)$$
$$E(*D*G*D*A)_a*D*G*D*E'; \quad (V)$$

wherein:

D denotes an alkyl diradical, an alkyl cycloalkyl diradical, a cycloalkyl diradical, an aryl diradical or an alkylaryl diradical having 6 to 30 carbon atoms;

G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

* denotes a urethane or ureido linkage;

a is at least 1;

A denotes a divalent polymeric radical of Formula VI:

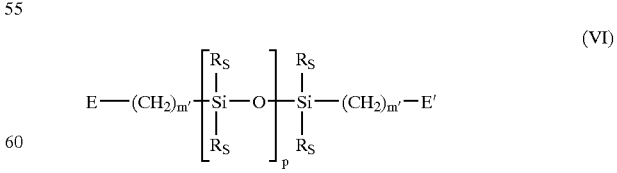
(VI)

wherein:
each $R_S$ independently denotes an alkyl or fluoro-substituted alkyl group having 1 to 10 carbon atoms which may contain ether linkages between carbon atoms;

m' is at least 1; and p is a number which provides a moiety weight of 400 to 10,000;

each of E and E' independently denotes a polymerizable unsaturated organic radical represented by Formula VII:

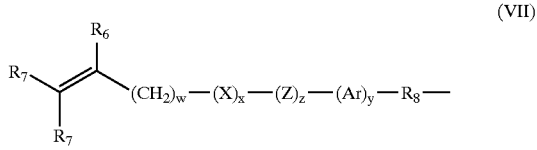

(VII)

wherein:

$R_6$ is hydrogen or methyl;

$R_7$ is hydrogen, an alkyl radical having 1 to 6 carbon atoms, or a —CO—Y—$R_9$ radical wherein Y is —O—, —S— or —NH—;

$R_8$ is a divalent alkylene radical having 1 to 10 carbon atoms;

$R_9$ is a alkyl radical having 1 to 12 carbon atoms;

X denotes —CO— or —OCO—;

Z denotes —O— or —NH—;

Ar denotes an aromatic radical having 6 to 30 carbon atoms;

w is 0 to 6; x is 0 or 1; y is 0 or 1; and z is 0 or 1.

A more specific example of a silicone-containing urethane monomer is represented by Formula (VIII):

the above structural formulas, U.S. Pat. No. 4,153,641 to Deichert et al. discloses additional unsaturated groups, including acryloxy or methacryloxy. Fumarate-containing materials such as those taught in U.S. Pat. Nos. 5,512,205; 5,449,729; and 5,310,779 to Lai are also useful substrates in accordance with the invention. Preferably, the silane macromonomer is a silicon-containing vinyl carbonate or vinyl carbamate or a polyurethane-polysiloxane having one or more hard-soft-hard blocks and end-capped with a hydrophilic monomer.

Specific examples of substrate materials useful in the present invention are taught in U.S. Pat. No. 5,908,906 to Künzler et al.; U.S. Pat. No. 5,714,557 to Künzler et al.; U.S. Pat. No. 5,710,302 to Künzler et al.; U.S. Pat. No. 5,708,094 to Lai et al.; U.S. Pat. No. 5,616,757 to Bambury et al.; U.S. Pat. No. 5,610,252 to Bambury et al.; U.S. Pat. No. 5,512,205 to Lai; U.S. Pat. No. 5,449,729 to Lai; U.S. Pat. No. 5,387,662 to Künzler et al. and UU.S. Pat. No. 5,310,779 to Lai; the disclosures of which are incorporated herein by reference.

As mentioned, the wetting agent is preferably a polymer containing carboxylic acid functionality, such as a polymer containing PAA. Accordingly, when the second device-forming monomer includes the epoxide reactive as the reactive functional group, the epoxide group (of the device-forming monomer) and the carboxlic acid group (of the wetting agent) react with one another to form a covalent bond therebetween. In addition, various carboxylic acid groups of the wetting agent that do not react with epoxide groups of the device also form a complex with electron

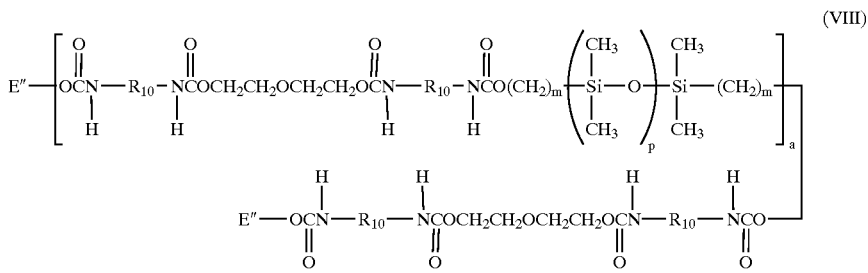

(VIII)

wherein m is at least 1 and is preferably 3 or 4, a is at least 1 and preferably is 1, p is a number which provides a moiety weight of 400 to 10,000 and is preferably at least 30, $R_{10}$ is a diradical of a diisocyanate after removal of the isocyanate group, such as the diradical of isophorone diisocyanate, and each E" is a group represented by:

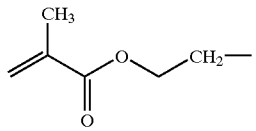

A preferred silicone hydrogel material comprises (in the bulk monomer mixture that is copolymerized) 5 to 50 percent, preferably 10 to 25, by weight of one or more silicone macromonomers, 5 to 75 percent, preferably 30 to 60 percent, by weight of one or more polysiloxanylalkyl (meth)acrylic monomers, and 10 to 50 percent, preferably 20 to 40 percent, by weight of a hydrophilic monomer. In general, the silicone macromonomer is a poly (organosiloxane) capped with an unsaturated group at two or more ends of the molecule. In addition to the end groups in donating moieties provided by the hydrophilic device-forming monomers, believed to be a hydrogen bonding complexation.

In addition to PAA-containing polymers, other wetting agent groups reactive with the second device-forming monomer reactive group include polymers containing sulfonic acid, fumaric acid, maleic acid, anhydride (such as maleic anhydride) and functionalized alcohol (such as vinyl alcohol) groups.

Specific surface coating wetting agents include P(vinylpyrrolidinone(VP)-co-acrylic acid(AA)), P(methylvinylether-alt-maleic acid), P(acrylic acid-graft-ethyleneoxide), P(acrylic acid-co-methacrylic acid), P(acrylamide-co-AA), P(acrylamide-co-AA), P(AA-co-maleic), and P(butadiene-maleic acid). Particularly preferred polymers are characterized by acid contents of at least about 30 mole percent, preferably at least about 40 mole percent. Especially preferred wetting agents are carboxylic acid-containing polymers, especially PAA-based polymers.

Therefore, according to preferred embodiments, the invention provides a method for the preparation of wettable silicone-based hydrogel formulations. Silicone hydrogel copolymers prepared from conventional hydrophilic monomers, N,Ndimethylacrylamide (DMA) or N,N- vinylpyrrolidinone (NVP), and an epoxide-containing device-forming monomer, are treated with water-based solutions including the PAA-containing wetting agent to render a lubricious, stable, highly wettable, durable PAA-based surface coating. The treatment may be performed at room temperature or under autoclave conditions. No additional oxidative surface treatment such as corona discharge or plasma oxidation is required. No separate coupling agent as described herein is required.

Solvents useful in the surface treatment (contacting) step of the present invention include solvents that readily solubilize proton donating solubes such as carboxylic acids, sulfonic acids, fumaric acid, maleic acids, anhydrides and functionalized vinyl alcohols. Preferred solvents include tetrahydrofuran (THF), acetonitrile, N,N-dimethyl formamide (DMF), and water. The most preferred solvent is water.

The surface treatment solution is preferably acidified before the contact step. Therefore, the pH of the solution is suitably less than 7, preferably less than 5 and more preferably less than 4. In a particularly preferred embodiment, the pH of the solution is about 3.5. For a discussion of the theory underlying the role of pH in complexation reactions in general, see *Advances in Polymer Science*, published by Springer-Verlag, Editor H. J. Cantow, et al, V45, 1982, pages 17–63.

The following examples illustrate various aspects of the present invention and should not be construed as limiting the invention.

EXAMPLE 1

A lens-forming monomer mixture was prepared by mixing the components listed in Table 1.

TABLE 1

Base Monomer Mixture A

| Component | Amount (pbw) |
|---|---|
| $M_2D_{25}$(40 TMS) | 20.0 |
| Tris | 24.5 |
| DMA | 17.5 |
| NVP | 17.5 |
| Hexanol | 20.0 |
| Initiator | 0.5 |

In Table 1, Tris denotes tris(trimethylsiloxy)silylpropyl methacrylate; DMA denotes N,N-dimethylacrylamide; NVP denotes N-vinyl-2-pyrrolidone; and pbw denotes parts by weight. The initiator is Darocur 1173™ initiator, and hexanol was employed as a diluent. Additionally, $M_2D_{25}$ (40TMS) denotes a mixture of the following two monomeric materials, at a molar ratio of 60/40, respectively:

Two additional monomer mixtures were obtained by adding glycidyl methacrylate, at 2 wt % and 4 wt %, to Base Monomer Mixture A. Glycidyl methacrylate is designated GMA in Table 2.

Each of the resultant monomer mixtures was cast into contact lenses by introducing the monomer mixture to a mold assembly composed of two polypropylene mold sections, the front mold section having a mold surface for forming a front contact lens surface and the back mold section having a mold surface for forming a back contact lens surface. Then, the mold section and monomer mixture were exposed to ultraviolet light to induce free radical polymerization and cure the monomer mixture to form a contact lens. The resultant contact lenses were removed from the mold assembly, and extracted to remove unreacted monomers.

The lenses were then placed in a 1 wt % solution (acidified to pH 3.5) of a copolymer of acrylamide and acrylic acid (30/70 molar ratio). The lenses in solution were subjected to a first autoclave cycle (30 minutes t 122° C./15 psi), the lenses were rinsed three times with distilled water, and then the lenses were placed in borate buffered saline and subjected to a second autoclave cycle.

The resultant treated lenses were highly wettable and lubricious. Various physical properties were measured and are reported in Table 2.

TABLE 2

| | Example 1-A | Example 1-B | Base Mixture A |
|---|---|---|---|
| GMA (wt %) | 4 | 2 | 0 |
| $O_2$ permeability (Dk) | — | — | 75 |
| % Water (wt %) | 36.3 | 36.0 | 36.2 |
| Modulus (g/mm$^2$) | 127 | 135 | 135 |
| Tensile strength (g/mm) | 41 | 43 | 39 |
| Tear strength (g/mm) | 3 | 2 | 2 |

EXAMPLE 2

A lens-forming monomer mixture was prepared by mixing the components listed in Table 3.

TABLE 3

Base Monomer Mixture B

| Component | Amount (pbw) |
|---|---|
| $V_2D_{90}F_{10}$ | 40.0 |
| TrisVC | 55.0 |
| NVP | 30.0 |
| Nonanol | 20.0 |
| Initiator | 0.5 |

In Table 3, TrisVC denotes 3-[tris(tri-methylsiloxy)silyl] propyl vinyl carbamate, and the remaining abbreviations are

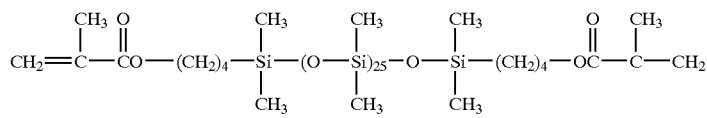

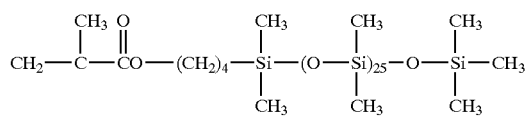

the same as above. The initiator is Darocur 1173™ initiator, and nonanol was employed as a diluent. Additionally, $V_2D_{90}F_{10}$ denotes the following monomeric material, where 10 mole % of the siloxane radicals are substituted with a fluorinated side chain (designated schematically as F1):

Various lenses were then placed in a 1 wt % solution (acidified to pH 3.5) of a copolymer of acrylamide and acrylic acid (30/70 molar ratio). The lenses in solution were subjected to a first autoclave cycle (30 minutes t 122° C./15 psi), the lenses were rinsed three times with distilled water,

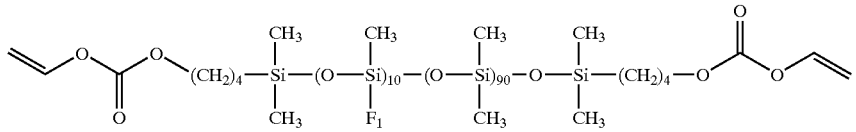

Three additional monomer mixtures were obtained by adding glycidyl vinyl carbonate, at 1 wt %, 2.5 wt % and 5 wt %, to Base Monomer Mixture B. Glycidyl vinyl carbonate is designated GVC in Table 4.

Each of the resultant monomer mixtures was cast into contact lenses by similar procedures as in Example 1. After removal from the mold assembly, the contact lenses were extracted with supercritical carbon dioxide.

The lenses were then placed in a 1 wt % solution (acidified to pH 3.5) of a copolymer of acrylamide and acrylic acid (30/70 molar ratio). The lenses in solution were subjected to a first autoclave cycle (30 minutes t 122° C./15 psi), the lenses were rinsed three times with distilled water, and then the lenses were placed in borate buffered saline and subjected to a second autoclave cycle.

The resultant treated lenses were highly wettable and lubricious. Various physical properties were measured and are reported in Table 4.

TABLE 4

|  | Base Mixture B | Ex 2-A | Ex 2-B | Ex 2-C |
|---|---|---|---|---|
| GVC (wt %) | 0 | 1 | 2.5 | 5 |
| $O_2$ permeability (Dk) | 190 | 171 | — | — |
| % Water (wt %) | 24.3 | 26.0 | 26.5 | 25.7 |
| Modulus (g/mm$^2$) | 66 | 49 | — | — |
| Tensile strength (g/mm) | — | 52 | — | — |
| Tear strength (g/mm) | 12 | 11 | — | — |

EXAMPLE 3

A lens-forming monomer mixture was prepared by mixing the components listed in Table 5.

TABLE 5

Base Monomer Mixture C

| Component | Amount (pbw) |
|---|---|
| PU-Si | 55.0 |
| Tris | 19.0 |
| DMA | 26.0 |
| Hexanol | 15.0 |
| Initiator | 0.5 |

In Table 5 PU-Si denotes a monomeric material of Formula (VIII), and the remaining abbreviations are the same as above. The initiator is Darocur 1173™ initiator, and hexanol was employed as a diluent.

Two additional monomer mixtures were obtained by adding glycidyl methacrylate, at 1 wt % and 2.5 wt %, to Base Monomer Mixture C.

Each of the resultant monomer mixtures was cast into contact lenses, and the contact lenses were processed, by similar procedures as in Example 1.

and then the lenses were placed in borate buffered saline and subjected to a second autoclave cycle. Various other lenses were not treated in any PAA-containing solution, designated in Table 7 as "control". The resultant treated lenses were highly wettable and lubricious.

TABLE 6-A

|  | Base Mixture C | Base Mixture C (control) |
|---|---|---|
| GMA (wt %) | 0 | 0 |
| $O_2$ permeability (Dk) | — | 115 |
| % Water (wt %) | 28.9 | 28.8 |
| Modulus (g/mm$^2$) | 53 | 63 |
| Tensile strength (g/mm) | 32 | 36 |
| Tear strength (g/mm) | 9 | 9 |

TABLE 6-B

|  | Example 3-A | Example 3-A (control) |
|---|---|---|
| GMA (wt %) | 1 | 1 |
| % Water (wt %) | 31.2 | 29.3 |
| Modulus (g/mm$^2$) | 45 | 52 |
| Tensile strength (g/mm) | 25 | 31 |
| Tear strength (g/mm) | — | — |

TABLE 6-C

|  | Example 3-B | Example 3-B (control) |
|---|---|---|
| GMA (wt %) | 2.5 | 2.5 |
| % Water (wt %) | 29.9 | 27.8 |
| Modulus (g/mm$^2$) | 38 | 57 |
| Tensile strength (g/mm) | 24 | 29 |
| Tear strength (g/mm) | — | — |

EXAMPLE 4

This examples illustrates the synthesis of additional wetting agents, namely reactive, hydrophilic copolymers of N,N-dimethylacrylamide (DMA) and methacrylic Acid (MA).

To a 3000 ml reaction flask were added distilled N,N-dimethylacrylamide (DMA, 128 g, 1.28 moles), methacrylic acid (MAA, 32 g, 0.37 moles) Vazo 64 (AIBN, 0.24 g, 0.0016 moles) and anhydrous 2-propanol (2000 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 72 hours. The volume of the reaction mixture was reduced to half by flash evaporation. The reactive polymer was precipitated into 8 L of ethyl ether and then collected by vacuum filtration. The solid was placed in a vacuum oven at 30° C. overnight to remove the ether leaving 142.34 g of reactive polymer (89% yield). The reactive polymer was placed in a desiccator for storage until use.

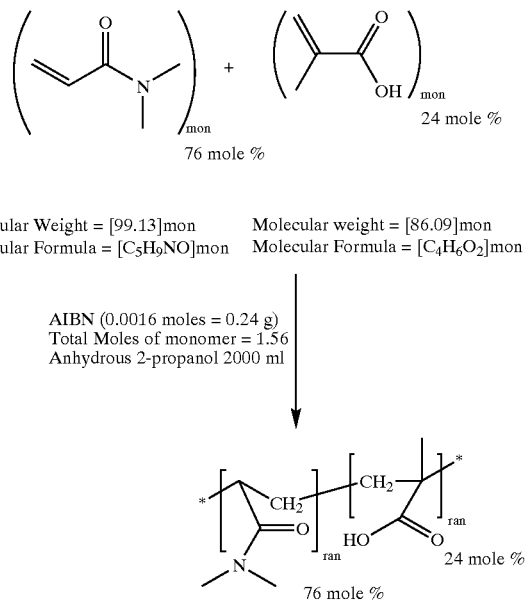

This general procedure was followed to prepare the reactive polymers listed in the table below.

TABLE 7

| DMA gram | DMA moles | DMA x mole % | MAA grams | MAA moles | MAA y mole % | AIBN moles | Solvent | volume ml | Time (hours) | Yield grams |
|---|---|---|---|---|---|---|---|---|---|---|
| 42 | 0.42 | 67 | 18 | 0.21 | 33 | 0.0006 | 2-propanol | 750 | 72 | 49.63 |
| 36 | 0.36 | 56 | 24 | 0.28 | 44 | 0.0006 | 2-propanol | 750 | 72 | 44.97 |

Many other modifications and variations of the present invention are possible in light of the teachings herein. It is therefore understood that, within the scope of the claims, the present invention can be practiced other than as herein specifically described.

What is claimed is:

1. A method for improving the wettability of a medical device, comprising:
   (a) providing a medical device formed from a monomer mixture comprising a hydrophilic device-forming monomer including a copolymerizable group and an electron donating moiety, and a second device-forming monomer including a copolymerizable group and a reactive functional group; and
   (b) contacting a surface of the medical device with a wetting agent including a proton donating moiety reactive with the functional group provided by the second device-forming monomer and that complexes with the electron donating moiety provided by the hydrophilic lens-forming monomer.

2. The method of claim 1, wherein the wetting agent comprises proton donating moieties selected from the group consisting of carboxylic acids, sulfonic acids, fumaric acids, maleic acids, anhydrides, and vinyl alcohols.

3. The method of claim 1 wherein said wetting agent comprises a polymer containing carboxylic acid reactive groups.

4. The method of claim 1, wherein the medical device comprises a silicone hydrogel, and the monomer mixture further comprises a silicone-containing device-forming monomer.

5. The method of claim 1, wherein the hydrophilic monomer is selected from the group consisting of vinyl lactams, acrylamides, vinyl carbonates, vinyl carbamates, and oxazolones.

6. The method of claim 5, wherein the hydrophilic monomer includes at least one member selected from the group consisting of N-vinylpyrrolidone and N,N-dimethylacrylamide.

7. The method of claim 1, wherein the second device-forming monomer includes a copolymerizable ethylenically unsaturated group and an epoxy reactive functional group.

8. The method of claim 7, wherein the second device-forming monomer is selected from the group consisting of glycidyl methacrylate, glycidyl acrylate, glycidyl vinylcarbonate, and glycidyl vinylcarbamate.

9. The method of claim 1, wherein the medical device has not been subjected to a surface oxidation treatment.

10. The method of claim 9, wherein the wetting agent forms a complex with the hydrophilic monomer in the absence of a surface oxidation treatment step and without the addition of a coupling agent.

11. The method of claim 10, wherein the wetting agent reacts with the proton donating moiety provided by the second lens-forming monomer in the absence of a surface oxidation treatment step and without the addition of a coupling agent.

12. The method of claim 1, wherein the medical device is an ophthalmic lens or ophthalmic implant.

13. The method of claim 11, wherein the medical device is a contact lens.

14. The method of claim 1, wherein the wetting agent includes a polymer having a carboxylic acid content of at least 30 mole percent.

15. The method of claim 1, wherein the wetting agent includes at least one member selected from the group consisting of P(vinylpyrolidinone(VP)-co-acrylic acid (AA)), P(methylvinylether-alt-maleic acid), P(acrylic acid-graft-ethyleneoxide), P(acrylic acid-co-methacrylic acid), P(acrylamide-co-AA), P(acrylamide-co-AA), P(AA-co-maleic), and P(butadiene-maleic acid).

16. The method of claim 1, wherein the wetting agent is present in a treatment solution having a pH of less than 5.

* * * * *